United States Patent
Sathe et al.

(10) Patent No.: US 11,510,909 B2
(45) Date of Patent: Nov. 29, 2022

(54) PHARMACEUTICAL COMPOSITION OF APIXABAN

(71) Applicant: UNICHEM LABORATORIES LTD., Mumbai Maharashtra (IN)

(72) Inventors: Dhananjay Sathe, Mumbai Maharashtra (IN); Srikant V. Pimple, Mumbai Maharashtra (IN); Pravin Kumar Maurya, Mumbai Maharashtra (IN); Dhananjay Pramod Tattu, Mumbai Maharashtra (IN); Milind Vinayak Sathe, Sr., Mumbai Maharashtra (IN)

(73) Assignee: UNICHEM LABORATORIES LTD., Mumbai Maharashtra (IN)

( * ) Notice: Subject to any disclaimer, the term of this patent is extended or adjusted under 35 U.S.C. 154(b) by 4 days.

(21) Appl. No.: 16/477,661

(22) PCT Filed: Feb. 1, 2018

(86) PCT No.: PCT/IB2018/050627
§ 371 (c)(1),
(2) Date: Jul. 12, 2019

(87) PCT Pub. No.: WO2018/150286
PCT Pub. Date: Aug. 23, 2018

(65) Prior Publication Data
US 2019/0358215 A1   Nov. 28, 2019

(30) Foreign Application Priority Data

Feb. 17, 2017  (IN) .............................. 201721005627
Feb. 17, 2017  (IN) .............................. 201721005628
Dec. 18, 2017  (IN) .............................. 201721045328

(51) Int. Cl.
*A61K 31/437*   (2006.01)
*A61K 31/4545*   (2006.01)
*A61K 9/20*   (2006.01)
*A61K 9/28*   (2006.01)

(52) U.S. Cl.
CPC .......... *A61K 31/437* (2013.01); *A61K 9/2018* (2013.01); *A61K 9/2027* (2013.01); *A61K 9/2054* (2013.01); *A61K 9/2077* (2013.01); *A61K 9/2095* (2013.01); *A61K 9/2866* (2013.01); *A61K 31/4545* (2013.01)

(58) Field of Classification Search
None
See application file for complete search history.

(56) References Cited

U.S. PATENT DOCUMENTS

| | | |
|---|---|---|
| 2009/0252787 A1 | 10/2009 | Pasha et al. |
| 2015/0272891 A1 | 10/2015 | Meergans et al. |
| 2015/0366810 A1 | 12/2015 | Kanamaru et al. |
| 2016/0243101 A1 | 8/2016 | Patel et al. |
| 2016/0346267 A1 * | 12/2016 | Stanic Ljubin .... A61K 31/4545 |

FOREIGN PATENT DOCUMENTS

WO   WO-2015121472 A1 *  8/2015  ........... A61K 9/2095

* cited by examiner

*Primary Examiner* — Bethany P Barham
*Assistant Examiner* — Barbara S Frazier
(74) *Attorney, Agent, or Firm* — Bacon & Thomas, PLLC

(57) ABSTRACT

The present disclosure relates to a stable, reproducible and bioequivalent apixaban compositions, wherein the composition comprising apixaban having a $D_{90}$ particle size of more than 100 microns, preferably between 300 and 1000 microns, and more preferably between 350 and 800 microns, and further comprising one or more pharmaceutically acceptable excipients. The present disclosure further provides a process for preparation of a pharmaceutical composition comprising apixaban by wet granulation.

5 Claims, No Drawings

PHARMACEUTICAL COMPOSITION OF APIXABAN

This application claims the benefit of priority of IN201721005627 filed on Feb. 17, 2017, and IN201721005628 filed on Feb. 17, 2017 and IN201721045328 filed on Dec. 18, 2017, the content of which are incorporated herein by reference in their entirety.

FIELD OF THE INVENTION

The present disclosure pertains to technical field of pharmaceuticals. In particular, the present disclosure pertains to a stable, reproducible and bioequivalent pharmaceutical composition of apixaban.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

Apixaban is chemically described as 1-(4methoxyphenyl)-7-oxo-6-[4-(2-oxopiperidin-1-yl)phenyl]-4,5,6,7-tetrahydro-1H-pyrazolo [3,4c]pyridine-3-carboxamide and is structurally represented by the formula shown below:

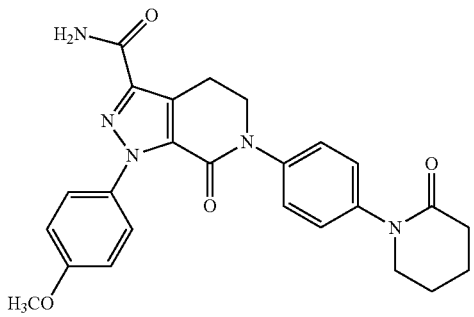 [SMILES: COc1ccc(-n2nc(C(N)=O)c3c2C(=O)N(c2ccc(N4CCCCC4=O)cc2)CC3)cc1]

Apixaban is marketed under brand name ELIQUIS®. It was approved by USFDA (US Food and Drug Administration) in December 2012 for treatment and secondary prophylaxis of deep vein thrombosis and pulmonary embolism. Apixaban is generically claimed in U.S. Pat. No. 6,413,980 and IN243917. It is specifically claimed in U.S. Pat. No. 6,967,208 and IN247381. U.S. Pat. No. 6,413,980 also claimed pharmaceutical composition of compounds disclosed therein. U.S. Pat. Nos. 6,413,980 and 6,967,208 are however silent on the stability aspects of the pharmaceutical composition and how to prepare the composition. They are also silent on the aspects of polymorphic stability of apixaban or any particle size distribution (PSD) specifications, either as compound or when present in the composition.

U.S. Pat. No. 9,326,945 claims a solid pharmaceutical composition comprising a therapeutically effective amount of crystalline apixaban particles and a pharmaceutically acceptable diluent or carrier, wherein the crystalline apixaban particles have a $D_{90}$ particle size equal to or less than about 89 µm, and wherein at least 77 wt % of apixaban dissolves within 30 minutes in a pH 6.8 phosphate buffer containing 0.05% sodium lauryl sulfate. This patent also specifically claims various dosage forms of apixaban, where apixaban with predefined $D_{90}$ is present in the composition. This patent stipulates that formulations that were made using a wet granulation process as well as those using large particles of apixaban drug substance resulted in less than optimal exposures, and that it can present quality control challenges. Therefore invention and guidance provided by U.S. Pat. No. 9,326,945 is that compositions for tablets comprising apixaban particles having a $D_{90}$ (90% of the volume) less than 89 µm lead to consistent in-vivo dissolution in humans (at physiologic pH). IN6587/DELNP/2012 guides in similar way.

US2015018386 and its equivalent IN592/MUM/2012 claim a composition and a process for preparation of a composition comprising an amorphous form of apixaban. WO2014027334 describes a composition of multiparticulate system.

WO2015121472 and US2016346267 describe a pharmaceutical composition comprising apixaban and a polymer having low viscosity as binder.

WO2015097090 and US2017000799 describe a solid particle of a poorly soluble drug, having an average particle size of 100 µm or less, wherein a solubilizer is adsorbed on the surface of the poorly soluble drug.

US20160143894 claims a pharmaceutical composition comprising crystalline form N-1 of apixaban having an X-ray powder diffraction pattern comprising peaks expressed in degrees 2θ (±0.2° 2θ) at 8.40, 12.80, 13.80, 16.90, 18.30, 21.00, 22.00, 24.70, 25.30, 26.80 and 32.60±0.2 2θ, having a mean particle size equal to or greater than 100 µm and one or more pharmaceutically acceptable excipients, diluents and carriers. Said application is silent about $D_{90}$ specifications of the apixaban. Secondly, although it has a general claim about composition, the entire specification is silent on bioavailability profile of the composition, or does not affirmatively state that the composition is bioequivalent to that of the reference listed drug ELIQUIS®. Although this reference has taught apixaban compositions, it has created severe restrictions in using apixaban. It is taught that if apixaban with $D_{90}$ of less than 89 µm is not used, it would result in inadequate exposure and the composition in which such apixaban is used would pose quality problems. In fact, that is the invention of the U.S. Pat. No. 9,326,945 patent. Thus there is severe limitation in using apixaban having $D_{90}$ more than 89 µm.

It is well known that increase in crystal size or particle jeopardizes the solubility of active ingredients. As has been described in the prior art references, it is the particle size distribution of the apixaban which is of critical importance to produce desirable composition. Therefore, as per the teachings of the prior art references, it is difficult to prepare a stable, reproducible and bioequivalent pharmaceutical composition if apixaban has a $D_{90}$ particle size of more than 89 µm.

Further, the apixaban compositions known hitherto, including the formulations described in U.S. Pat. No. 9,326,945, require binders to impart integrity to the structure of the compositions and to facilitate the formation of compressible mass, to assist the flow of contents on tabletting or pelleting machines. Often flow problems or hardness problems are experienced if binders are not used in designing the pharmaceutical compositions especially tablets, granules and capsules. These problems are of higher intensity when the material to be processed is fluffy or has lower bulk density.

Based on the above, there still exists a need in the art for an improved pharmaceutical composition and dosage form comprising apixaban and improved technological process for the preparation thereof.

The present disclosure satisfies the existing needs, as well as others, and generally overcomes the deficiencies found in the prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability.

OBJECT OF THE INVENTION

It is an object of the present disclosure to provide a stable and reproducible pharmaceutical composition comprising apixaban.

It is another object of the present disclosure to provide a pharmaceutical composition of apixaban allowing for the oral administration of therapeutically effective dosage of apixaban, while exhibiting chemical and physical stability.

It is another object of the present disclosure to provide a pharmaceutical composition of apixaban which provides desired oral bioavailability of apixaban when ingested.

It is another object of the present disclosure to provide a pharmaceutical composition of apixaban, which is bioequivalent to the marketed apixaban product.

It is yet another object of the present disclosure to provide a process for preparation of a stable, reproducible and bioequivalent pharmaceutical composition of apixaban.

SUMMARY OF THE INVENTION

According to one aspect of the present disclosure there is provided a pharmaceutical composition comprising apixaban having a $D_{90}$ particle size of more than 100 microns and one or more pharmaceutically acceptable excipients. In various embodiments, the pharmaceutical composition disclosed herein can be a tableting composition which can maintain its form with or without the use of a binder.

In an embodiment, the $D_{90}$ particle size of apixaban can be in the range of 300 to 1000 microns. Preferably, the $D_{90}$ particle size of apixaban can be between 350 and 800 microns.

In one embodiment, the one or more pharmaceutically acceptable excipients that can be used in the pharmaceutical composition of the present disclosure can include a diluent, a binder, a surfactant, a disintegrant, a lubricant, a glidant, a coating agent, a plasticizer, a coloring agent, and a viscosity enhancer.

According to another aspect of the present disclosure there is provided a process for preparation of a pharmaceutical composition comprising apixaban, wherein the process can include the steps of: preparing granules comprising apixaban having a $D_{90}$ particle size of more than 100 microns by wet granulation; adding one or more pharmaceutically acceptable excipients to the granules to obtain a mixture; and converting the mixture into a suitable dosage form. Suitable dosage forms can include, but not limited to, tablet, capsule, powder, caplet, granules, pellets, tablet in tablet, tablet in capsule, pellets in capsule, powder in capsule, and granules in capsule.

In preferred embodiments, the pharmaceutical composition can be formulated into tablets which can include a mixture of apixaban, at least one diluent, at least one disintegrant, at least one lubricant, and at least one surfactant. In some embodiments, the tablet can further include at least one binder in an amount sufficient to form a tablet. In some other embodiments, the tablet can be obtained without using any binder. In certain preferred embodiments, the resulting uncoated core tablets can subsequently be film coated. The film coating can include Opadry yellow or pink.

Various objects, features, aspects and advantages of the inventive subject matter will become more apparent from the following detailed description of preferred embodiments.

DETAILED DESCRIPTION OF THE INVENTION

The following is a detailed description of embodiments of the present disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, formulation conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

Various terms are used herein. To the extent a term used in a claim is not defined below, it should be given the broadest definition persons in the pertinent art have given that term as reflected in printed publications and issued patents at the time of filing.

Terms "microns" or mu·m or μ or mum or μm are used interchangeably and mean the same. The term "composition" as used herein refers to equivalents thereof, including but not limited to cores, coated cores, pellets, micro-pellets, pills, compressed tablets, granules, spheres, capsules and the like.

The term "pharmaceutically acceptable" as used herein means that which is useful in preparing a pharmaceutical composition that is generally safe and non-toxic.

The term "tablet" is intended to encompass compressed pharmaceutical dosage forms of all shape and size, whether coated or uncoated.

The term "stable and reproducible" as used herein means that the composition is stable when stored at stability conditions as per ICH stability guidelines and that the process described when followed, produces a stable and bioequivalent formulation repeatedly.

The term "bioequivalent" as used herein means that a formulation that has the same pharmacologic potency and bioavailability as that of reference formulation containing same active agent at the same dose. Two products or formulations containing the same active ingredient are bioequivalent if their rates and extents of absorption i.e., bioavailability are the same The term 'similarity factor' or 'f2 factor' as used herein refers to one way of comparing dissolution profiles of two different products. This model-independent mathematical approach compares the dissolution profile of the two products: test and reference or two strengths. Tests are recommended to be performed under the same test conditions. The dissolution time points for both the profiles should be the same. An f2 value of 50 or greater (50-100) ensures sameness or equivalence of two curves, and thus equivalent performance of the two products, in-vitro.

Embodiments of the present disclosure relate to a stable, reproducible and bioequivalent pharmaceutical composition comprising apixaban having a $D_{90}$ particle size of more than 100 microns, and one or more pharmaceutically acceptable excipients. In various embodiments, the pharmaceutical composition of the present disclosure can be a tableting composition which can maintain its form with or without the use of a binder.

As used herein, $D_{90}$ particle size more than 100 microns is to be interpreted as apixaban having $D_{90}$ particle size from 100 microns to 1000 microns. In an embodiment, the $D_{90}$ particle size of apixaban can be in the range of from 300 to 1000 microns. Preferably, the $D_{90}$ particle size of apixaban can be between 350 and 800 microns. According to embodiments of the present disclosure, apixaban produced in bulk drug plant can be milled and micronized to obtain apixaban having a $D_{90}$ particle size of more than 100 microns.

In one embodiment, the one or more pharmaceutically acceptable excipients that can be used in the pharmaceutical composition of the present disclosure can include a diluent, a binder, a surfactant, a disintegrant, a lubricant, a glidant, a coating agent, a plasticizer, a coloring agent, and a viscosity enhancer.

In a preferred embodiment, the pharmaceutical composition of the present disclosure can include apixaban having a D90 particle size of more than 100 microns, in combination with at least one diluent, at least one disintegrant, at least one lubricant, at least one surfactant, and optionally at least one binder.

In an exemplary embodiment, the diluent can be selected from the group consisting of microcrystalline cellulose, microfine cellulose, powdered cellulose, lactose, dibasic calcium phosphate, tribasic calcium phosphate, starch, pregelatinized starch, calcium carbonate, calcium sulfate, magnesium carbonate, magnesium oxide, dextrates, dextrin, dextrose, kaolin, maltodextrin, mannitol, sucrose, methyl dextrin, sorbitol, and a combination thereof.

Examples of binder can include, but are not limited to, cellulose derivatives such as hydroxypropyl cellulose, hydroxypropylmethylcellulose, sodium carboxy methyl cellulose, methyl cellulose and ethyl cellulose, polyvinylpyrrolidone, polyethyleneglycol, polyvinyl alcohols, pregelatinized starch, starch paste, sucrose, glucose, acacia, tragacanth, gelatin, alginic acid, sodium alginate, and a combination thereof.

Examples of disintegrant can include, but not limited to, carboxymethylcellulose calcium, carboxymethylcellulose sodium, croscarmellose sodium, crospovidone, polacrilin potassium, sodium alginate, sodium starch glycolate, and a combination thereof.

Examples of lubricant can include, but not limited to, magnesium stearate, aluminium stearate, sucrose stearate, calcium stearate stearic acid, talc, fumaric acid, palmitic acid, sodium stearyl fumarate, glyceryl monostearate, carnauba wax, hydrogenated vegetable oils, mineral oil, polyethylene glycols, and a combination thereof.

Examples of surfactant can include, but not limited to, self-emulsifying glyceryl monooleate, docusate sodium, emulsifying wax BP, sodium lauryl sulfate (SLS), benzethonium chloride, cetrimide, cetylpyridinium chloride, lauric acid, myristyl alcohol, sorbic acid, emulsifying wax, glyceryl monooleate, phospholipids, polyoxyethylene alkyl ethers (macrogol cetostearyl ether, macrogol lauryl ether, macrogol oleyl ether, macrogol stearyl ether), polyoxyethylene castor oil derivatives (macrogolglycerol ricinoleate, macrogolglycerol hydroxystearate), polyoxyethylene sorbitan fatty acid esters (polysorbate 20, 40, 60, and 80), polyoxyethylene stearates, polyoxylglycerides (caprylocaproyl polyoxylglycerides, lauroyl polyoxylglycerides, linoleoyl polyoxylglycerides, oleoyl polyoxylglycerides and stearoyl polyoxylglycerides), sorbitan esters (sorbitan laurate, sorbitan oleate, sorbitan palmitate, sorbitan sesquioleate, sorbitan stearate, sorbitan trioleate), triethyl citrate, and a combination thereof.

Novelty of apixaban having a $D_{90}$ particle size of more than 100 microns, preferably in the range of 300 to 1000 microns, and more preferably in the range of 350 to 800 microns resides in the fact that it was not reported in the prior art that Apixaban having a $D_{90}$ particle size of more than 100 microns produces stable, reproducible, and bioequivalent pharmaceutical composition.

Non-obviousness of the invention resides in the fact that in light of prior art teachings, nobody would ever imagine that apixaban having a $D_{90}$ particle size of more than 100 microns, preferably in the range of 300 to 1000 microns and more preferably in the range of 350 to 800 microns would ever produce stable, reproducible and bioequivalent pharmaceutical composition. Prior art does teach wet granulation of apixaban. But it severely and categorically limits the use of wet granulation of apixaban having $D_{90}$ as prescribed in U.S. Pat. No. 9,326,945.

In another aspect, the present disclosure provides a process for preparation of the pharmaceutical composition of the present disclosure, wherein the process can include the steps of: preparing granules comprising apixaban having a $D_{90}$ particle size of more than 100 microns by wet granulation; adding one or more pharmaceutically acceptable excipients to the granules to obtain a mixture; and converting the mixture into a suitable dosage form. Suitable dosage forms can include, but not limited to, tablet, capsule, powder, caplet, granules, pellets, tablet in tablet, tablet in capsule, pellets in capsule, powder in capsule, and granules in capsule.

In preferred embodiments, the pharmaceutical composition can be formulated into tablets which can include a mixture of apixaban, at least one diluent, at least one disintegrant, at least one lubricant, and at least one surfactant. In some embodiments, the tablet can further include at least one binder in an amount sufficient to form a tablet. In some other embodiments, the tablet can be obtained without using any binder. In certain preferred embodiments, the resulting uncoated core tablets can subsequently be film coated. The film coating can include Opadry yellow or pink.

In one embodiment, the present disclosure provides a binder-free process for preparing a pharmaceutical composition of apixaban, the process can include the steps of:
co-sifting a diluent and a disintegrant through a sieve to prepare a dry mix;
dissolving apixaban having a $D_{90}$ particle size of more than 100 microns in an organic solvent to prepare a drug solution;
spraying the drug solution onto the dry mix in a fluidized bed processor to produce drug granules;
drying the drug granules in a fluidized bed processor to produce dried drug granules;
spraying a solution of a surfactant onto the dried drug granules to produce surfactant coated drug granules;
drying the surfactant coated drug granules in a fluidized bed processor to prepare dried surfactant coated drug granules;
sifting the dried surfactant coated drug granules through a sieve to produce sifted granules;
pre-lubricating the sifted granules to produce an extragranular pre-lubricated blend; lubricating the extragranular pre-lubricated blend to produce a lubricated blend; and
compressing the lubricated blend to produce an uncoated tablet.

In one embodiment of the binder-free process, the uncoated tablet is coated with a film coating such as for example, Opadry yellow or pink.

In one embodiment of the binder-free process, the dry mix can be prepared by co-sifting the diluent and the disintegrant through a #40 sieve. Preferably, the diluent can be microcrystalline cellulose, lactose anhydrous, or a combination thereof. More preferably, the diluent can be a combination of microcrystalline cellulose and lactose anhydrous, and the disintegrant can be croscarmellose sodium.

In an exemplary embodiment of the binder-free process, the organic solvent that can be used to produce the drug solution can be methylene chloride, isopropyl alcohol or a mixture thereof.

In one embodiment of the binder-free process, sifted granules can be produced by sifting the dried surfactant coated drug granules through a #30 sieve.

In one embodiment of the binder-free process, the extragranular pre-lubricated blend can be produced by pre-lubricating the sifted granules with croscarmellose sodium.

In one embodiment of the binder-free process, the lubricated blend can be produced by lubricating the extragranular pre-lubricated blend with magnesium stearate.

In one embodiment of the binder-free process, the solution of surfactant can be an aqueous solution of surfactant, which can be prepared by dissolving a predetermined quantity of a surfactant such as sodium lauryl sulphate in a predetermined volume of purified water.

In one embodiment, sifted granules can be produced by using binder solution which is prepared by dissolving binder and surfactant in purified water and top sprayed on contents of fluidized bed processor.

In another embodiment, the present disclosure provides a process for preparing a pharmaceutical composition of apixaban using a binder, the process can include the steps of:
co-sifting a diluent and a disintegrant through a sieve to prepare a dry mix;
mixing a surfactant, a binder and a purified water to produce a binder solution;
dispersing apixaban having a $D_{90}$ particle size of more than 100 microns in the binder solution to produce a drug solution;
spraying the drug solution onto the dry mix in a Rapid Mixer Granulator (RMG) to produce drug granules;
drying the drug granules in a rapid dryer to produce dried drug granules;
sifting the dried drug granules through a sieve to produce sifted granules;
pre-lubricating the sifted granules to produce pre-lubricated granules;
lubricating the pre-lubricated granules to produce a lubricated blend;
compressing the lubricated blend to produce an uncoated tablet; and
optionally coating the uncoated tablet.

In one embodiment of this process, the dry mix can be prepared by co-sifting the diluent and the disintegrant through a #40 sieve. Preferably, the diluent can be microcrystalline cellulose, lactose anhydrous, or a combination thereof. More preferably, the diluent can be a combination of microcrystalline cellulose and lactose anhydrous, and the disintegrant can be croscarmellose sodium.

In one embodiment of this process, sifted granules can be produced by sifting the dried drug granules through a #30 sieve.

In one embodiment of this process, the binder can be polyvinylpyrrolidone, and the surfactant can be sodium lauryl sulphate.

The relative % of the ingredients used may be selected as per related FDA guidelines for lower strengths.

The pharmaceutical composition comprising apixaban having a $D_{90}$ particle size of more than 100 microns, preferably in the range of 300 to 1000 microns, and more preferably in the range of 350 to 800 microns provides a stable, reproducible and binder-free formulation which shows similarity factor value of more than 50 when dissolution of the formulation is compared with marketed apixaban product ELIQUIS. Also when different strengths are compared, f2 value or similarity factor value of more than 50 is observed. When in-vivo testing and comparison is done, the composition of the present invention shows similarity factor of more than 50 when compared with innovator product ELIQUIS.

In various embodiments, the pharmaceutical composition of the present disclosure can be in the form of a tablet, capsule, powder, disc, caplet, granules, pellets, tablet in tablet, tablet in capsule, pellets in capsule, powder in capsule, granules in capsule and other like dosage forms suitable for oral administration. The tablets may further be coated with film forming polymers. Tablets may optionally be coated with a film coat, which provides an aesthetic appeal. Film coat also provides moisture protection, taste masking etc. Coating agents include, but not limited to Opadry®. Preferred Opadry® is Opadry II Pink (32K540052).

In another embodiment, the present disclosure provides a process for preparation of pharmaceutical composition comprising apixaban having a $D_{90}$ particle size of more than 100 microns, preferably in the range of 300 to 1000 microns and more preferably in the range of 350 to 800 microns by wet granulation process, wherein the process includes co-sifting of apixaban with other ingredients and wet granulating it, followed by drying, lubricating and compressing. The process can optionally include a binder for granulation or compression. Multiple Bioequivalence Studies proved that the compositions prepared as per the invention are stable, reproducible and bioequivalent.

While the foregoing description discloses various embodiments of the disclosure, other and further embodiments of the invention may be devised without departing from the basic scope of the disclosure. The invention is not limited to the described embodiments, versions or examples, which are included to enable a person having ordinary skill in the art to make and use the invention when combined with information and knowledge available to the person having ordinary skill in the art.

EXAMPLES

The present disclosure is further explained in the form of following examples. However, it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Example 1

Apixaban produced in bulk drug plant, having far bigger particle is milled and or micronized to produce Apixaban having a $D_{90}$ particle size of more than 100 microns, preferably between 300 and 1000 microns and more preferably between 350 and 800 microns. Milling and micronization is carried out by known equipments such as multimill. The PSD is determined by Malvern Mastersizer 2000. Wet methods using liquid paraffin or sunflower oil are useful.

Example 2

| S. No. | Ingredient | mg/Tablet 5 mg | mg/Tablet 2.5 mg | % |
|---|---|---|---|---|
| | Part I (Dry Mix/Intra-granular) | | | |
| 1 | Microcrystalline Cellulose | 82 | 41 | 41% |
| 2 | Lactose Anhydrous | 101.5 | 50.75 | 50.75% |
| 3 | Croscarmellose Sodium | 4 | 2 | 2% |
| | Part-II (Drug Solution) | | | |
| 4 | Apixaban (D90 ≥ 100 micron) | 5 | 2.5 | 2.5% |
| 5 | Methylene Chloride | q.s. | q.s. | — |
| 6 | Iso Propyl Alcohol | q.s. | q.s. | — |
| | Part-III (Surfactant Solution) | | | |
| 7 | Sodium Lauryl Sulphate | 2 | 1 | 1% |
| 8 | Purified Water | q.s. | q.s. | — |
| | Part -IV (Pre-lubrication/Extra-granular) | | | |
| 9 | Croscarmellose Sodium | 4 | 2 | 2% |
| | Part -V (Lubrication/Extra-granular) | | | |
| 10 | Magnesium Stearate | 1.5 | 0.75 | 0.75% |
| | Total Weight of Core Tablet | 200 | 100 | 100% |
| | Part- VI (Coating) | | | |
| 11 | Opadry Pink/Yellow | 6 | 3 | |
| 12 | Purified Water | q.s. | q.s. | |
| | Total Weight of Coated Tablet | 206 | 103 | |

Manufacturing Process:
  a) Part-I (Dry Mix): MCC (microcrystalline cellulose), lactose anhydrous, croscarmellose sodium was sifted through #40 sieve and mixed to prepare the dry mix.
  b) Part-II: Apixaban was added to MDC (Methylene Chloride) under stirring to form clear solution, then IPA (isopropyl alcohol) was added and stirred. This is clear drug solution. Clear drug solution of Apixaban is sprayed on dry mix prepared in Part-I in FBP (Fluidised Bed Processor) by top spray method.
  c) Part-III: SLS (sodium lauryl sulphate) was dissolved in purified water to form clear surfactant solution.
  Surfactant solution spraying: clear surfactant solution is sprayed on contents of fluidised bed processor by top spray, to prepare the granules.
  d) Drying and sizing: Granules were dried in fluidised bed processor for 15 minutes and sized using #30 sieve.
  e) Pre-Lubrication: Croscarmellose sodium was sifted through #40 sieve and in double cone blender, sized granules prepared in step d) were pre-lubricated to prepare pre-lubricated blend.
  f) Lubrication: magnesium stearate was sifted through #60 sieve and pre-lubricated blend prepared in step e) was lubricated to prepare lubricated blend.
  g) Compression: lubricated blend prepared in step f) was compressed into tablets using appropriate punch set.
  h) Coating: compressed tablet prepared in step g) were coated by Opadry pink/yellow suspension to achieve required weight gain for different strengths.

Wherein diluent such as lactose anhydrous when incorporated purely intragranularly or when incorporated intragranularly as well as extragranularly produces bioequivalent composition.

Example 3

Composition comprising Apixaban of the PSD $D_{90}$ more than 100μ, preferably between 300 and 1000 microns, and more preferably between 350 and 800 microns.

| Sr. No | Ingredient | mg/Tablet For 5 mg | mg/Tablet For 2.5 mg | % |
|---|---|---|---|---|
| | Part I (Dry Mix/Intra-granular) | | | |
| 1 | Apixaban ($D_{90} \geq$ 100 micron) | 1 | 0.5 | 0.5% |
| 2 | Microcrystalline Cellulose | 82 | 41 | 41% |
| 3 | Lactose Anhydrous | 101.5 | 50.75 | 50.75% |
| 4 | Croscarmellose Sodium | 4 | 2 | 2% |
| | Part-II (Drug Solution) | | | |
| 5 | Apixaban ($D_{90} \geq$ 100 micron) | 4 | 2 | 2% |
| 6 | Methylene Chloride | q.s. | q.s. | — |
| 7 | Iso Propyl Alcohol | q.s. | q.s. | — |
| | Part-III (Surfactant Solution) | | | |
| 8 | Sodium Lauryl Sulphate | 2 | 1 | 1% |
| 9 | Purified Water | q.s. | q.s. | — |
| | Part -IV (Pre-lubrication/Extra-granular) | | | |
| 10 | Croscarmellose Sodium | 4 | 2 | 2.% |
| | Part -V (Lubrication/Extra-granular) | | | |
| 11 | Magnesium Stearate | 1.5 | 0.75 | 0.75% |
| | Total Weight of Core Tablet | 200 | 100 | 100% |
| | Part -VI (Coating) | | | |
| 12 | Opadry | 6 | 3 | |
| 13 | Purified Water | q.s. | q.s. | |
| | Total Weight of Coated Tablet | 206 | 103 | |

Manufacturing Process:
a. Part-I: Apixaban, MCC (microcrystalline cellulose), lactose anhydrous, croscarmellose sodium was sifted through #40 sieve and mixed to prepare dry mix.
b. Part-II: Apixaban was added to MDC (Methylene Chloride) under stirring to form clear solution, then IPA (iso propyl alcohol) was added and stirred. This is clear drug solution. Clear drug solution of Apixaban is sprayed on dry mix prepared in Part-I in FBP (fluidised bed processor) by top spray.
c. Part-III: sodium lauryl sulphate was dissolved in purified water under stirring to form clear surfactant solution. Clear surfactant solution sprayed on contents of fluidised bed processor by top spray, to prepare the granules.
d. Drying and sizing: granules was dried in fluidised bed processor for 15 minutes and sized by using #30 sieve.
e. Pre-Lubrication: croscarmellose sodium was sifted through #40 sieve and in double cone blender, sized granules prepared in step d) were pre-lubricated to prepare pre-lubricated blend.
f. Lubrication: magnesium stearate was sifted through #60 sieve and and pre-lubricated blend prepared in step e) was lubricated to prepare lubricated blend.
g. Compression: Lubricated blend prepared in step f) was compressed into tablets by using appropriate punch set.
h. Coating: Compressed tablet prepared in step g) were coated by Opadry suspension to achieve required weight gain.

Example 4

Binder free composition comprising Apixaban of the PSD D90 more than 100 microns, preferably between 300 and 1000 microns and more preferably between 350 and 800 microns

| S. No. | Ingredient | mg/Tablet 5 mg | mg/Tablet 2.5 mg | % |
|---|---|---|---|---|
| | Part I (Dry Mix/Intra-granular) | | | |
| 1 | Microcrystalline Cellulose | 82 | 41 | 41% |
| 2 | Lactose Anhydrous | 101.5 | 50.75 | 50.75% |
| 3 | Croscarmellose Sodium | 4 | 2 | 2% |
| | Part-II (Drug Solution) | | | |
| 4 | Apixaban (D90 ≥ 100 micron) | 5 | 2.5 | 2.5% |
| 5 | Methylene Chloride | q.s. | q.s. | — |
| 6 | Iso Propyl Alcohol | q.s. | q.s. | — |
| | Part-III (Surfactant Solution) | | | |
| 7 | Sodium Lauryl Sulphate | 2 | 1 | 1% |
| 8 | Purified Water | q.s. | q.s. | — |
| | Part -IV (Pre-lubrication/Extra-granular) | | | |
| 9 | Croscarmellose Sodium | 4 | 2 | 2% |
| | Part -V (Lubrication/Extra-granular) | | | |
| 10 | Magnesium Stearate | 1.5 | 0.75 | 0.75% |
| | Total Weight of Core Tablet | 200 | 100 | 100% |
| | Part -VI (Coating) | | | |
| 11 | Opadry Pink/Yellow | 6 | 3 | |
| 12 | Purified Water | q.s. | q.s. | |
| | Total Weight of Coated Tablet | 206 | 103 | |

Manufacturing Process:
a) Part-I (Dry Mix): MCC (Microcrystalline cellulose), lactose anhydrous, croscarmellose sodium was sifted through #40 sieve and mixed to prepare the dry mix.
b) Part-II: Apixaban was added to MDC (Methylene Chloride) under stirring to form clear solution, then IPA (Isopropyl alcohol) was added and stirred. This is clear drug solution. Clear drug solution of Apixaban is sprayed on dry mix prepared in Part-I in FBP (Fluidised Bed Processor) by Top Spray method.
c) Part-III: SLS was dissolved in Purified water to form clear Surfactant solution. Surfactant solution spraying: Clear Surfactant solution is sprayed on contents of Fluidised Bed Processor by Top Spray, to prepare the granules.
d) Drying and sizing: Granules were dried in Fluidised Bed Processor for 15 minutes and sized using #30 sieve.
e) Pre-Lubrication: croscarmellose sodium was sifted through #40 sieve and in double cone blender, sized granules prepared in step d) were pre-lubricated to prepare pre-lubricated blend.
f) Lubrication: magnesium stearate was sifted through #60 sieve and pre-lubricated blend prepared in step e) was lubricated to prepare lubricated blend.

g) Compression: Lubricated blend prepared in step f) was compressed into tablets using appropriate punch set.

h) Coating: Compressed tablet prepared in step g) were coated by Opadry pink/yellow suspension to achieve required weight gain for different strengths.

Wherein diluent such as Lactose Anhydrous when incorporated purely intragranularly or when incorporated intragranularly as well as extragranularly produces bioequivalent composition.

Example 5

Binder free composition comprising Apixaban of the PSD $D_{90}$ more than 100 microns, preferably between 300 and 1000 microns, and more preferably between 350 and 800 microns.

| Sr No | Ingredient | mg/Tablet For 5 mg | mg/Tablet For 2.5 mg | % |
|---|---|---|---|---|
|  | Part I (Dry Mix/ Intra-granular) |  |  |  |
| 1 | Apixaban ($D_{90} \geq$ 100 micron) | 1 | 0.5 | 0.5% |
| 2 | Microcrystalline Cellulose | 82 | 41 | 41% |
| 3 | Lactose Anhydrous | 101.5 | 50.75 | 50.75% |
| 4 | Croscarmellose Sodium | 4 | 2 | 2% |
|  | Part-II (Drug Solution) |  |  |  |
| 5 | Apixaban ($D_{90} \geq$ 100 micron) | 4 | 2 | 2% |
| 6 | Methylene Chloride | q.s. | q.s. | — |
| 7 | Iso Propyl Alcohol | q.s. | q.s. | — |
|  | Part-III (Surfactant Solution) |  |  |  |
| 8 | Sodium Lauryl Sulphate | 2 | 1 | 1% |
| 9 | Purified Water | q.s. | q.s. | — |
|  | Part -IV (Pre-lubrication/ Extra-granular) |  |  |  |
| 10 | Croscarmellose Sodium | 4 | 2 | 2% |
|  | Part -V (Lubrication/ Extra-granular) |  |  |  |
| 11 | Magnesium Stearate | 1.5 | 0.75 | 0.75% |
|  | Total Weight of Core Tablet | 200 | 100 | 100% |
|  | Part -VI (Coating) |  |  |  |
| 12 | Opadry | 6 | 3 |  |
| 13 | Purified Water | q.s. | q.s. |  |
|  | Total Weight of Coated Tablet | 206 | 103 |  |

Manufacturing Process:
a. Part-I: Apixaban, MCC (Microcrystalline cellulose), lactose anhydrous, croscarmellose sodium was sifted through #40 sieve and mixed to prepare dry mix.
b. Part-II: Apixaban was added to MDC (Methylene Chloride) under stirring to form clear solution, then IPA (Isopropyl alcohol) was added and stirred. This is clear drug solution. Clear drug solution of Apixaban is sprayed on dry mix prepared in Part-I in FBP (Fluidized Bed Processor) by top spray.
c. Part-III: Sodium lauryl sulphate was dissolved in Purified water under stirring to form clear surfactant solution. Clear surfactant solution sprayed on contents of Fluidised Bed Processor by Top Spray, to prepare the granules.
d. Drying and sizing: Granules was dried in Fluidised Bed Processor for 15 minutes and sized by using #30 sieve.
e. Pre-Lubrication: Croscarmellose sodium was sifted through #40 sieve and in double cone blender, sized granules prepared in step d) were pre-lubricated to prepare pre-lubricated blend.
f. Lubrication: magnesium stearate was sifted through #60 sieve and and pre-lubricated blend prepared in step e) was lubricated to prepare lubricated blend.
g. Compression: Lubricated blend prepared in step f) was compressed into tablets by using appropriate punch set.
h. Coating: Compressed tablet prepared in step g) were coated by Opadry suspension to achieve required weight gain.

Example 6

Comparison of In-Vitro Dissolution Profile

Apixaban tablets were prepared as per the composition and procedure depicted in Example 2/3 with Innovator ELIQUIS and were subjected to dissolution studies.

Table 1 (a-d): Provide comparative dissolution profiles of ELIQUIS 5 mg RLD (5F82427A) versus Apixaban Tablet 5 mg (GAPH 16004) as per composition of Example 2.

TABLE 1-a

Official dissolution method: 0.05M Sodium Phosphate Buffer with 0.05% SLS, pH 6.8, USP Apparatus II (Paddle), 75 RPM

| | Time Point | | | | | | | |
|---|---|---|---|---|---|---|---|---|
| | 0 | 5 | 10 | 20 | 30 | 45 | F2 (inclu. 5 min) | F2 (Exclu. 5 min) |
| ELIQUIS (5F82427A) | 0 | 71 | 86 | 91 | 93 | 93 | 72 | 82 |
| Apixaban (16004) | 0 | 78 | 88 | 94 | 95 | 95 | | |

TABLE 1-b 0.1N HCl, USP Apparatus II (Paddle), 75 RPM

| | Time Point | | | | | | | |
|---|---|---|---|---|---|---|---|---|
| | 0 | 5 | 10 | 20 | 30 | 45 | F2 (inclu. 5 min) | F2 (Exclu. 5 min) |
| ELIQUIS (5F82427A) | 0 | 54 | 77 | 88 | 92 | 95 | 57 | 82 |
| Apixaban (16004) | 0 | 70 | 81 | 89 | 92 | 94 | | |

TABLE 1-c 4.5 pH Acetate Buffer, USP Apparatus II (Paddle), 75 RPM

| | Time Point | | | | | | | |
|---|---|---|---|---|---|---|---|---|
| | 0 | 5 | 10 | 20 | 30 | 45 | F2 (inclu. 5 min) | F2 (Exclu. 5 min) |
| ELIQUIS (5F82427A) | 0 | 63 | 88 | 93 | 95 | 96 | 60 | 94 |
| Apixaban (16004) | 0 | 77 | 87 | 93 | 96 | 97 | | |

TABLE 1-d 6.8 pH Phosphate Buffer, USP Apparatus II (Paddle), 75 RPM

| | Time Point | | | | | | |
|---|---|---|---|---|---|---|---|
| | 0 | 5 | 10 | 20 | 30 | 45 | F2 (Inclu. 5 min) | F2 (Exclu. 5 min) |
| ELIQUIS (5F82427A) | 0 | 66 | 81 | 89 | 93 | 96 | 68 | 83 |
| Apixaban (16004) | 0 | 75 | 84 | 91 | 93 | 94 | | |

Table 2 (a-d): Comparative dissolution profiles of Apixaban Tablet 5 mg (GAPH 16004) v/s Apixaban Tablet 2.5 mg (GAPL 16004) as per composition of Example 2.

TABLE 2-A 0.05M Sodium Phosphate Buffer with 0.05% SLS, pH 6.8, USP Apparatus II (Paddle), 75 RPM at temperature 37° C.

| | Time Point | | | | | | | |
|---|---|---|---|---|---|---|---|---|
| | 0 | 5 | 10 | 20 | 30 | 45 | F2 (Inclu. 5 min) | F2 (Exclu. 5 min) |
| Apixaban Tablet 5 mg GAPH 16004 | 0 | 78 | 88 | 94 | 95 | 95 | 79 | 86 |
| Apixaban Tablet 2.5 mg GAPL 16004 | 0 | 82 | 91 | 95 | 96 | 96 | | |

TABLE 2-b 0.1N HCl, USP Apparatus II (Paddle), 75 RPM

| | Time Point | | | | | | | |
|---|---|---|---|---|---|---|---|---|
| | 0 | 5 | 10 | 20 | 30 | 45 | F2 (Inclu. 5 min) | F2 (Exclu. 5 min) |
| Apixaban Tablet 5 mg GAPH 16004 | 0 | 70 | 81 | 89 | 92 | 94 | 78 | 89 |
| Apixaban Tablet 2.5 mg GAPL 16004 | 0 | 75 | 83 | 90 | 92 | 93 | | |

TABLE 2-c 4.5 pH Acetate Buffer, USP Apparatus II (Paddle), 75 RPM

| | Time Point | | | | | | | |
|---|---|---|---|---|---|---|---|---|
| | 0 | 5 | 10 | 20 | 30 | 45 | F2 (Inclu. 5 min) | F2 (Exclu. 5 min) |
| Apixaban Tablet 5 mg GAPH 16004 | 0 | 77 | 87 | 93 | 96 | 97 | 82 | 81 |
| Apixaban Tablet 2.5 mg GAPL 16004 | 0 | 79 | 87 | 92 | 93 | 94 | | |

TABLE 2-d 6.8 pH Phosphate Buffer, USP Apparatus II (Paddle), 75 RPM

| | Time Point | | | | | | | |
|---|---|---|---|---|---|---|---|---|
| | 0 | 5 | 10 | 20 | 30 | 45 | F2 (Inclu. 5 min) | F2 (Exclu. 5 min) |
| Apixaban Tablet 5 mg GAPH 16004 | 0 | 75 | 84 | 91 | 93 | 94 | 90 | 96 |
| Apixaban Tablet 2.5 mg GAPL 16004 | 0 | 77 | 85 | 91 | 93 | 94 | | |

Example 7

In-Vivo Comparison of Apixaban 5 mg Tablets Prepared as Per the Invention with Reference Listed Drug ELIQUIS Apixaban tablets comprising Apixaban having $D_{90}$ more than 89 μm were prepared as per example 2 and were subjected to bioequivalence studies using reference listed drug ELIQUIS. The findings are summarized in tables below:

A] Bioequivalence Study Under Fasting Conditions:

This is a single-dose, crossover, open-label two period Study in two groups of 35 subjects. Test product A (Apixaban) and Reference product B (ELIQUIS) was used for study.

TABLE NO 1

Bioequivalence Summary Table of Cmax

| Treatment | Ratio | 90% CI |
|---|---|---|
| Test product A/Innovator Product B | 91.63 | (86.39, 97.18) |

TABLE NO 2

Bioequivalence Summary Table of AUC0-t

| Treatment | Ratio | 90% CI |
|---|---|---|
| Test product A/Innovator Product B | 94.50 | (90.20, 99.01) |

TABLE NO 3

Bioequivalence Summary Table of AUC0_inf

| Treatment | Ratio | 90% CI |
|---|---|---|
| Test product A/Innovator Product B | 94.73 | (90.45, 99.22) |

B] Bioequivalence Study Under Fed Conditions:

This is a single-dose, crossover, open-label two period Study in two groups of 23 subjects. Test product A (Apixaban) and Reference product B (ELIQUIS) was used for study.

TABLE 1

Bioequivalence Summary Table of Cmax

| Treatment | Ratio | 90% CI |
|---|---|---|
| Test product A/Innovator Product B | 100.66 | (93.43, 108.46) |

TABLE 2

Bioequivalence Summary Table of AUC0-t

| Treatment | Ratio | 90% CI |
|---|---|---|
| Test product A/Innovator Product B | 95.95 | (91.39, 100.73) |

TABLE 3

Bioequivalence Summary Table of AUC0_inf

| Treatment | Ratio | 90% CI |
|---|---|---|
| Test product A/Innovator Product B | 95.61 | (91.09, 100.35) |

Example 8

A] One More Fasting Bioequivalence Study
Summary Table 1 of Cmax

| Treatment | Ratio | 90% CI |
|---|---|---|
| Test product A [Example 2]/Innovator Product C | 98.99 | (93.68, 104.59) |
| Test product B [Example 3]/Innovator Product C | 85.17 | (80.60, 89.99) |

TABLE 2

Bioequivalence Summary Table of AUC last

| Treatment | Ratio | 90% CI |
|---|---|---|
| Test product A [Example 2]/Innovator Product C | 96.87 | (88.19, 106.40) |
| Test product B [Example 3]/Innovator Product C | 93.69 | (85.29, 102.91) |

TABLE 3

Bioequivalence Summary Table of AUC0_inf

| Treatment | Ratio | 90% CI |
|---|---|---|
| Test product A [Example 2]/Innovator Product C | 96.38 | (86.48, 107.40) |
| Test product B [Example 3]/Innovator Product C | 95.10 | (85.34, 105.98) |

B] One More Fed Bioequivalence Study: Summary Table 1 of Cmax

| Treatment | Ratio | 90% CI |
|---|---|---|
| Test product A [Example 2]/Innovator Product C | 100.04 | (91.34, 109.57) |
| Test product B [Example 3]/Innovator Product C | 101.22 | (92.41, 110.86) |

TABLE 2

Bioequivalence Summary Table of AUC last

| Treatment | Ratio | 90% CI |
|---|---|---|
| Test product A [Example 2]/Innovator Product C | 105.12 | (99.19, 111.40) |
| Test product B [Example 3]/Innovator Product C | 96.95 | (91.48, 102.75) |

TABLE 3

Bioequivalence Summary Table of AUC0_inf

| Treatment | Ratio | 90% CI |
|---|---|---|
| Test product A [Example 2]/Innovator Product C | 104.97 | (99.17, 111.09) |
| Test product B [Example 3]/Innovator Product C | 97.36 | (91.99, 103.04) |

Example 9

Stability Profile of Apixaban 5 mg Tablets of the Invention

Accelerated stability data of Apixaban Tablets 5 mg [B.No: API (353)036B, HDPE pack]

| Sr. No. | | | | | 40° C./75% RH | | | |
|---|---|---|---|---|---|---|---|---|
| | Dissolution Time points | Limits | Initial | 1M | 2M | 3M | 6M | |
| 1 | 10 minutes | NLT 75% (Q) in 30 mins | 92% | 86% | 80% | 89% | 76% | |
| | 20 minutes | | 94% | 92% | 88% | 93% | 86% | |
| | 30 minutes | | 95% | 94% | 92% | 94% | 89% | |
| | 45 minutes | | 95% | 95% | 93% | 96% | 92% | |
| 2 | Related substances (%) | | | | | | | |
| a. | Unknown Impurities | NMT 0.20% | 0.01, 0.01 | 0.01, 0.01 | 0.01, 0.01 | 0.02, 0.02 | 0.01, 0.01 | |
| b. | Total Impurities ≥ 0.05% | NMT 1.5% | BRT | BRT | BRT | BRT | BRT | |
| 3 | Assay | 90 to 110% | 96.2% | 99.0% | 97.3% | 96.9% | 97.1% | |

There was no significant change in description.
BRT: Below reporting threshold

Example 10

Stability Profile of Apixaban 2.5 mg Tablets of the Invention

Accelerated stability data of Apixaban Tablets 2.5 mg [B.No: API(353)036A, HDPE pack]

| Sr. No. | Dissolution Time points | Limits | Initial | 40° C./75% RH | | | |
|---|---|---|---|---|---|---|---|
| | | | | 1M | 2M | 3M | 6M |
| 1 | 10 minutes | NLT 75% | 91% | 80% | 80% | 76% | 77% |
| | 20 minutes | (Q) | 94% | 89% | 89% | 85% | 86% |
| | 30 minutes | in 30 mins | 95% | 92% | 92% | 89% | 89% |
| | 45 minutes | | 94% | 95% | 95% | 93% | 90% |
| 2 | | Related substances (%) | | | | | |
| a. | Unknown Impurities | NMT 0.20% | 0.01, 0.01 | 0.01, 0.01 | 0.01, 0.01 | 0.02, 0.01 | 0.02, 0.04 |
| b. | Total Impurities ≥ 0.05% | NMT 1.5% | BRT | BRT | BRT | BRT | BRT |
| 3 | Assay | 90 to 110% | 94.7% | 95.5% | 93.6% | 100.1% | 95.0% |

There was no significant change in description.
BRT: Below reporting threshold

Example 11

Comparison of In-Vitro Dissolution Profile

The tablets of Apixaban having $D_{90}$ more than 100µ, more preferably more than 300µ to 1000µ and most preferably more than 350µ to 800µ were prepared as per the composition and procedure depicted in Example 4/5 with Innovator ELIQUIS and were subjected to dissolution studies.

Table 1 (a-d): Provides comparative dissolution profiles of ELIQUIS 5 mg RLD (5F82427A) versus Apixaban Tablet 5 mg (GAPH 16004) as per composition of Example 4 in 900 ml 0.05 M Sodium Phosphate Buffer with 0.05% SLS, pH 6.8, USP Apparatus II (Paddle), 75 RPM at temperature 37° C.

TABLE 1-a

Official dissolution method: 0.05M Sodium Phosphate Buffer with 0.05% SLS, pH 6.8, USP Apparatus II (Paddle)

| | Time Point | | | | | | |
|---|---|---|---|---|---|---|---|
| | 0 | 5 | 10 | 20 | 30 | 45 | F2 (inclu. 5 min) | F2 (Exclu. 5 min) |
| ELIQUIS (5F82427A) | 0 | 71 | 86 | 91 | 93 | 93 | 72 | 82 |
| Apixaban (16004) | 0 | 78 | 88 | 94 | 95 | 95 | | |

TABLE 1-b 0.1N HCl, USP Apparatus II (Paddle), 75 RPM

| | Time Point | | | | | | | |
|---|---|---|---|---|---|---|---|---|
| | 0 | 5 | 10 | 20 | 30 | 45 | F2 (inclu. 5 min) | F2 (Exclu. 5 min) |
| ELIQUIS (5F82427A) | 0 | 54 | 77 | 88 | 92 | 95 | 57 | 82 |
| Apixaban (16004) | 0 | 70 | 81 | 89 | 92 | 94 | | |

TABLE 1-c 4.5 pH Acetate Buffer, USP Apparatus II (Paddle), 75 RPM

| | Time Point | | | | | | | |
|---|---|---|---|---|---|---|---|---|
| | 0 | 5 | 10 | 20 | 30 | 45 | F2 (inclu. 5 min) | F2 (Exclu. 5 min) |
| ELIQUIS (5F82427A) | 0 | 63 | 88 | 93 | 95 | 96 | 60 | 94 |
| Apixaban (16004) | 0 | 77 | 87 | 93 | 96 | 97 | | |

TABLE 1-d 6.8 pH Phosphate Buffer, USP Apparatus II (Paddle), 75 RPM

| | Time Point | | | | | | | |
|---|---|---|---|---|---|---|---|---|
| | 0 | 5 | 10 | 20 | 30 | 45 | F2 (inclu. 5 min) | F2 (Exclu. 5 min) |
| ELIQUIS (5F82427A) | 0 | 66 | 81 | 89 | 93 | 96 | 68 | 83 |
| Apixaban (16004) | 0 | 75 | 84 | 91 | 93 | 94 | | |

Table 2 (a-d): Comparative dissolution profiles of Apixaban Tablet 5 mg (GAPH 16004) v/s Apixaban Tablet 2.5 mg (GAPL 16004) as per composition of Example 4.

TABLE 2-a 0.05M Sodium Phosphate Buffer with 0.05% SLS, pH 6.8, USP Apparatus II (Paddle), 75 RPM at temperature 37° C.

| | Time Point | | | | | | | |
|---|---|---|---|---|---|---|---|---|
| | 0 | 5 | 10 | 20 | 30 | 45 | F2 (Inclu. 5 min) | F2 (Exclu. 5 min) |
| Apixaban Tablet 5 mg GAPH 16004 | 0 | 78 | 88 | 94 | 95 | 95 | 79 | 86 |
| Apixaban Tablet 2.5 mg GAPL 16004 | 0 | 82 | 91 | 95 | 96 | 96 | | |

TABLE 2-b 0.1N HCl, USP Apparatus II (Paddle), 75 RPM

| | Time Point | | | | | | |
|---|---|---|---|---|---|---|---|
| | 0 | 5 | 10 | 20 | 30 | 45 | F2 (Inclu. 5 min) | F2 (Exclu. 5 min) |
| Apixaban Tablet 5 mg GAPH 16004 | 0 | 70 | 81 | 89 | 92 | 94 | 78 | 89 |
| Apixaban Tablet 2.5 mg GAPL 16004 | 0 | 75 | 83 | 90 | 92 | 93 | | |

TABLE 2-c 4.5 pH Acetate Buffer, USP Apparatus II (Paddle), 75 RPM

| | Time Point | | | | | | |
|---|---|---|---|---|---|---|---|
| | 0 | 5 | 10 | 20 | 30 | 45 | F2 (Inclu. 5 min) | F2 (Exclu. 5 min) |
| Apixaban Tablet 5 mg GAPH 16004 | 0 | 77 | 87 | 93 | 96 | 97 | 82 | 81 |
| Apixaban Tablet 2.5 mg GAPL 16004 | 0 | 79 | 87 | 92 | 93 | 94 | | |

TABLE 2-d 6.8 pH Phosphate Buffer USP Apparatus II (Paddle), 75 RPM

| | Time Point | | | | | | |
|---|---|---|---|---|---|---|---|
| | 0 | 5 | 10 | 20 | 30 | 45 | F2 (Inclu. 5 min) | F2 (Exclu. 5 min) |
| Apixaban Tablet 5 mg GAPH 16004 | 0 | 75 | 84 | 91 | 93 | 94 | 90 | 96 |
| Apixaban Tablet 2.5 mg GAPL 16004 | 0 | 77 | 85 | 91 | 93 | 94 | | |

Example 12

In-Vivo Comparison of Apixaban 5 mg Tablets Prepared as Per the Invention with Reference Listed Drug ELIQUIS Apixaban tablets comprising Apixaban having $D_{90}$ more than 89 mum were prepared as per example 4 and were subjected to bioequivalence studies using reference listed drug ELIQUIS. The findings are summarized in tables below:

A] Bioequivalence Study Under Fasting Conditions:

This is a single-dose, crossover, open-label two period Study in two groups. Test product A (Apixaban) and Reference product B (ELIQUIS) was used.

TABLE NO 1

Bioequivalence Summary Table of Cmax

| Treatment | Ratio | 90% CI |
|---|---|---|
| Test product A/Innovator Product B | 91.63 | ( 86.39, 97.18) |

TABLE NO 2

Bioequivalence Summary Table of AUC0_t

| Treatment | Ratio | 90% CI |
|---|---|---|
| Test product A/Innovator Product B | 94.50 | ( 90.20, 99.01) |

TABLE NO 3

Bioequivalence Summary Table of AUC0_inf

| Treatment | Ratio | 90% CI |
|---|---|---|
| Test product A/Innovator Product B | 94.73 | ( 90.45, 99.22) |

B] Bioequivalence Study Under Fed Conditions:

This is a single-dose, crossover, open-label two period Study in two groups. Test product A (Apixaban) and Reference product B (ELIQUIS) was used for study.

TABLE 1

Bioequivalence Summary Table of Cmax

| Treatment | Ratio | 90% CI |
|---|---|---|
| Test product A/Innovator Product B | 100.66 | (93.43, 108.46) |

TABLE 2

Bioequivalence Summary Table of AUC0_t

| Treatment | Ratio | 90% CI |
|---|---|---|
| Test product A/Innovator Product B | 95.95 | (91.39, 100.73) |

TABLE 3

Bioequivalence Summary Table of AUC0_inf

| Treatment | Ratio | 90% CI |
|---|---|---|
| Test product A/Innovator Product B | 95.61 | ( 91.09, 100.35) |

Example 13

A] One More Fasting Bioequivalence Study Summary Table 1 of Cmax

| Treatment | Ratio | 90% CI |
|---|---|---|
| Test product A [Example 2]/Innovator Product C | 98.99 | (93.68, 104.59) |
| Test product B [Example 3]/Innovator Product C | 85.17 | (80.60, 89.99) |

TABLE 2

Bioequivalence Summary Table of AUC last

| Treatment | Ratio | 90% CI |
|---|---|---|
| Test product A [Example 2]/Innovator Product C | 96.87 | ( 88.19, 106.40) |
| Test product B [Example 3]/Innovator Product C | 93.69 | ( 85.29, 102.91) |

TABLE 3

Bioequivalence Summary Table of AUC0_inf

| Treatment | Ratio | 90% CI |
|---|---|---|
| Test product A [Example 2]/Innovator Product C | 96.38 | (86.48, 107.40) |
| Test product B [Example 3]/Innovator Product C | 95.10 | (85.34, 105.98) |

B] One More Fed Bioequivalence Study: Summary Table 1 of Cmax

| Treatment | Ratio | 90% CI |
|---|---|---|
| Test product A [Example 2]/Innovator Product C | 100.04 | (91.34, 109.57) |
| Test product B [Example 3]/Innovator Product C | 101.22 | (92.41, 110.86) |

TABLE 2

Bioequivalence Summary Table of AUC last

| Treatment | Ratio | 90% CI |
|---|---|---|
| Test product A [Example 2]/Innovator Product C | 105.12 | (99.19, 111.40) |
| Test product B [Example 3]/Innovator Product C | 96.95 | (91.48, 102.75) |

TABLE 3

Bioequivalence Summary Table of AUC0_inf

| Treatment | Ratio | 90% CI |
|---|---|---|
| Test product A [Example 2]/Innovator Product C | 104.97 | (99.17, 111.09) |
| Test product B [Example 3]/Innovator Product C | 97.36 | (91.99, 103.04) |

Example 14

Stability Profile of Apixaban 5 mg Tablets of the Invention

Accelerated stability data of Apixaban Tablets 5 mg [B.No: API (353)036B, HDPE pack]

| Sr. No. | Dissolution Time points | Limits | Initial | 40° C./75% RH | | | |
|---|---|---|---|---|---|---|---|
| | | | | 1M | 2M | 3M | 6M |
| 1 | 10 minutes | NLT 75% (Q) in 30 mins | 92% | 86% | 80% | 89% | 76% |
| | 20 minutes | | 94% | 92% | 88% | 93% | 86% |
| | 30 minutes | | 95% | 94% | 92% | 94% | 89% |
| | 45 minutes | | 95% | 95% | 93% | 96% | 92% |
| 2 | Related substances (%) | | | | | | |
| a. | Unknown Impurities | NMT 0.20% | 0.01, 0.01 | 0.01, 0.01 | 0.01, 0.02 | 0.02, 0.02 | 0.01, 0.01 |
| b. | Total Impurities ≥ 0.05% | NMT 1.5% | BRT | BRT | BRT | BRT | BRT |
| 3 | Assay | 90 to 110% | 96.2% | 99.0% | 97.3% | 96.9% | 97.1% |

There was no significant change in description.
BRT: Below reporting threshold

Example 15

Stability Profile of Apixaban 2.5 mg Tablets of the Invention

Accelerated stability data of Apixaban Tablets 2.5 mg [B.No: API (353)036A, HDPE pack]

| Sr. No. | Dissolution Time points | Limits | Initial | 40° C./75% RH | | | |
|---|---|---|---|---|---|---|---|
| | | | | 1M | 2M | 3M | 6M |
| 1 | 10 minutes | NLT 75% (Q) in 30 mins | 91% | 80% | 80% | 76% | 77% |
| | 20 minutes | | 94% | 89% | 89% | 85% | 86% |
| | 30 minutes | | 95% | 92% | 92% | 89% | 89% |
| | 45 minutes | | 94% | 95% | 95% | 93% | 90% |
| 2 | Related substances (%) | | | | | | |
| a. | Unknown Impurities | NMT 0.20% | 0.01, 0.01 | 0.01, 0.01 | 0.01, 0.01 | 0.02, 0.01 | 0.02, 0.04 |
| b. | Total Impurities ≥ 0.05% | NMT 1.5% | BRT | BRT | BRT | BRT | BRT |
| 3 | Assay | 90 to 110% | 94.7% | 95.5% | 93.6% | 100.1% | 95.0% |

There was no significant change in description.
BRT: Below reporting threshold

Example 16

Wet Granulation Method (by Using Fluidized Bed Processor)

| Sr. No. | Ingredients | 5 mg (mg/Tab) | 2.5 mg (mg/Tab) | % w.r.t. core tab | % w.r.t. coated tab |
|---|---|---|---|---|---|
| | Part I (Dry Mix/Intra-granular) | | | | |
| 1 | Microcrystalline Cellulose | 79 | 39.5 | 39.5 | 38.35 |
| 2 | Lactose Anhydrous | 98.5 | 49.25 | 49.25 | 47.82 |
| 3 | Croscarmellose Sodium | 4 | 2 | 2 | 1.94 |
| | Part-II (Drug Solution) | | | | |
| 4 | Apixaban (D90 ≥ 100 micron) | 5 | 2.5 | 2.5 | 2.43 |
| 5 | Methylene Chloride* | q.s. | q.s. | — | — |
| 6 | Iso Propyl Alcohol* | q.s. | q.s. | — | — |
| | Part-III (Binder Solution) | | | | |
| 7 | Sodium Lauryl Sulphate | 2 | 1 | 1 | 0.97 |
| 8 | Polyvinylpyrrolidone (Povidone K-25) | 6 | 3 | 3 | 2.91 |
| 9 | Purified Water* | q.s. | q.s. | — | — |
| | Part -IV (Pre-lubrication/Extra-granular) | — | — | — | — |
| 10 | Croscarmellose Sodium | 4 | 2 | 2 | 1.94 |
| | Part -V(Lubrication/Extra-granular) | | | | |
| 11 | Magnesium Stearate | 1.5 | 0.75 | 0.75 | 0.73 |
| | Total Weight of Core Tablet | 200 | 100 | 100 | — |
| | Part -VI (Coating) | — | — | — | — |
| 12 | Opadry Pink/Yellow | 6 | 3 | — | 2.91 |
| 13 | Purified Water* | q.s. | q.s. | — | — |
| | Total Weight of Coated Tablet | 206 | 103 | — | 100 |

*Removed during processing & only traces will be present in final product Manufacturing process:

a) Part-I (Dry Mix): Microcrystalline Cellulose, Lactose Anhydrous, Croscarmellose sodium were sifted through #40 sieve and mixed to prepare the dry mix.
b) Part-II: Apixaban was added to MDC under stirring to form clear solution, then IPA was added and stirred. Clear drug solution of Apixaban was sprayed on dry mix prepared in Part-I in FBP by Top Spray method.
c) Part-III: SLS and Povidone K-25 were dissolved in Purified water to form binder solution. Binder solution spraying: solution is sprayed on contents of Fluidized Bed Processor by Top Spray, to prepare the granules.
d) Drying and sizing: Granules were dried in Fluidized Bed Processor for 15 minutes and sized using #30 sieve.
e) Pre-Lubrication: Croscarmellose Sodium was sifted through # 40 sieve and in Double Cone Blender, sized granules prepared in step d) were Pre-Lubricated to prepare pre-lubricated blend.
f) Lubrication: Magnesium Stearate was sifted through # 60 sieve and pre-lubricated blend prepared in step e) was lubricated to prepare lubricated blend.
g) Compression: Lubricated blend prepared in step f) was compressed into tablets using appropriate punch set.
h) Coating: Compressed tablets prepared in step g) were coated by Opadry pink/yellow suspension to achieve required weight gain for different strengths.

Example 17

Wet Granulation Method (by Using Fluidized Bed Processor)

| Sr. No. | Ingredients | 5 mg (mg/Tab) | 2.5 mg (mg/Tab) | % w.r.t. core tab | % w.r.t. coated tab |
|---|---|---|---|---|---|
| | Part I (Dry Mix/Intra-granular) | | | | |
| 1 | Apixaban (D90 ≥ 100 micron) | 4 | 2 | 2 | 1.94 |
| 2 | Microcrystalline Cellulose | 79 | 39.5 | 39.5 | 38.35 |
| 3 | Lactose Anhydrous | 98.5 | 49.25 | 49.25 | 47.82 |
| 4 | Croscarmellose Sodium | 4 | 2 | 2 | 1.94 |
| | Part-II (Drug Solution) | — | — | — | — |
| 5 | Apixaban (D90 ≥ 100 micron) | 1 | 0.5 | 0.5 | 0.49 |
| 6 | Methylene Chloride* | q.s. | q.s. | — | — |
| 7 | Iso Propyl Alcohol* | q.s. | q.s. | — | — |
| | Part-III (Binder Solution) | — | — | — | — |
| 8 | Sodium Lauryl Sulphate | 2 | 1 | 1 | 0.97 |
| 9 | Polyvinylpyrrolidone (Povidone K-25) | 6 | 3 | 3 | 2.91 |
| 10 | Purified Water* | q.s. | q.s. | — | — |
| | Part -IV (Pre-lubrication/Extra-granular) | — | — | — | — |

| Sr. No. | Ingredients | 5 mg (mg/Tab) | 2.5 mg (mg/Tab) | % w.r.t. core tab | % w.r.t. coated tab |
|---|---|---|---|---|---|
| 11 | Croscarmellose Sodium | 4 | 2 | 2 | 1.94 |
|  | Part -V(Lubrication/Extra-granular) | — | — | — | — |
| 12 | Magnesium Stearate | 1.5 | 0.75 | 0.75 | 0.73 |
|  | Total Weight of Core Tablet | 200 | 100 | 100 | — |
|  | Part -VI (Coating) | — | — | — | — |
| 13 | Opadry Pink/Yellow | 6 | 3 | — | 2.91 |
| 14 | Purified Water* | q.s. | q.s. | — | — |
|  | Total Weight of Coated Tablet | 206 | 103 | — | 100 |

*Removed during processing & only traces will be present in final product Manufacturing process:

a) Part-I (Dry Mix): Apixaban, Microcrystalline Cellulose, Lactose anhydrous, Croscarmellose sodium were sifted through #40 sieve and mixed to prepare the dry mix.
b) Part-II: Apixaban was added to MDC under stirring to form clear solution, then IPA was added and stirred. Clear drug solution of Apixaban was sprayed on dry mix prepared in Part-I in FBP by Top Spray method.
c) Part-III: Sodium Lauryl Sulphate and Povidone K-25 were dissolved in Purified water to form binder solution. Binder solution spraying: solution is sprayed on contents of Fluidized Bed Processor by Top Spray, to prepare the granules.
d) Drying and sizing: Granules were dried in Fluidized Bed Processor for 15 minutes and sized using #30 sieve.
e) Pre-Lubrication: Croscarmellose Sodium was sifted through # 40 sieve and in Double Cone Blender, sized granules prepared in step d) were Pre-Lubricated to prepare pre-lubricated blend.
f) Lubrication: Magnesium Stearate was sifted through # 60 sieve and pre-lubricated blend prepared in step e) was lubricated to prepare lubricated blend.
g) Compression: Lubricated blend prepared in step f) was compressed into tablets using appropriate punch set.
h) Coating: Compressed tablets prepared in step g) were coated by Opadry pink/yellow suspension to achieve required weight gain for different strengths.

Example 18

Wet Granulation Method (by Using Rapid Mixer Granulator)

| Sr. No. | Ingredients | 5 mg (mg/Tab) | 2.5 mg (mg/Tab) | % w.r.t. core tab | % w.r.t. coated tab |
|---|---|---|---|---|---|
|  | Part I (Dry Mix/Intra-granular) |  |  |  |  |
| 1 | Microcrystalline Cellulose | 79 | 39.5 | 39.5 | 38.35 |
| 2 | Lactose Anhydrous | 98.5 | 49.25 | 49.25 | 47.82 |
| 3 | Croscarmellose Sodium | 4 | 2 | 2 | 1.94 |
|  | Part-II (Binder/Drug dispersion) | — | — | — | — |
| 4 | Apixaban (D90 ≥ 100 micron) | 5 | 2.5 | 2.5 | 2.43 |
| 5 | Sodium Lauryl Sulphate | 2 | 1 | 1 | 0.97 |
| 6 | Polyvinylpyrrolidone (Povidone K-25) | 6 | 3 | 3 | 2.91 |
| 7 | Purified Water* | q.s. | q.s. | — | — |
|  | Part -III (Pre-lubrication/Extra-granular) | — | — | — | — |
| 8 | Croscarmellose Sodium | 4 | 2 | 2 | 1.94 |
|  | Part-IV(Lubrication/Extra-granular) | — | — | — | — |
| 9 | Magnesium Stearate | 1.5 | 0.75 | 0.75 | 0.73 |
|  | Total Weight of Core Tablet | 200 | 100 | 100 | — |
|  | Part -V (Coating) | — | — | — | — |
| 10 | Opadry Pink/yellow | 6 | 3 | — | 2.91 |
| 11 | Purified Water* | q.s. | q.s. | — | — |
|  | Total Weight of Coated Tablet | 206 | 103 | — | 100 |

*Removed during processing & only traces will be present in final product. Manufacturing process:

a) Part-I (Dry Mix): Microcrystalline Cellulose, Lactose Anhydrous, Croscarmellose sodium were sifted through #40 sieve and mixed to prepare the dry mix.
b) Part-II: Sodium lauryl sulphate and Povidone K-25 were dissolved in water. Apixaban was dispersed in obtained solution. This dispersion was sprayed on dry mix prepared in step a) in RMG to prepare the granules.
c) Drying and sizing: Granules were dried in rapid dryer for 15 minutes and sized using #30 sieve.
d) Pre-Lubrication: Croscarmellose Sodium was sifted through # 40 sieve and in Double Cone Blender, sized granules prepared in step c) were pre-Lubricated to prepare pre-lubricated blend.
e) Lubrication: Magnesium Stearate was sifted through # 60 sieve and pre-lubricated blend prepared in step d) was lubricated to prepare lubricated blend.
f) Compression: Lubricated blend prepared in step e) was compressed into tablets using appropriate punch set.
g) Coating: Compressed tablets prepared in step f) were coated by Opadry pink/yellow suspension to achieve required weight gain for different strengths.

Example 19

Wet Granulation Method (by Using Rapid Mixer Granulator)

| Sr. No. | Ingredients | 5 mg (mg/Tab) | 2.5 mg (mg/Tab) | % w.r.t. core tab | % w.r.t. coated tab |
|---|---|---|---|---|---|
| | Part I (Dry Mix/Intra-granular) | | | | |
| 1 | Apixaban (D90 ≥ 100 micron) | 4 | 2 | 2 | 1.94 |
| 2 | Microcrystalline Cellulose | 79 | 39.5 | 39.5 | 38.35 |
| 3 | Lactose Anhydrous | 98.5 | 49.25 | 49.25 | 47.82 |
| 4 | Croscarmellose Sodium | 4 | 2 | 2 | 1.94 |
| | Part-II (Binder/Drug dispersion) | — | — | — | — |
| 5 | Apixaban (D90 ≥ 100 micron) | 1 | 0.5 | 0.5 | 0.49 |
| 6 | Sodium Lauryl Sulphate | 2 | 1 | 1 | 0.97 |
| 7 | Polyvinylpyrrolidone (Povidone K-25) | 6 | 3 | 3 | 2.91 |
| 8 | Purified Water* | q.s. | q.s. | — | — |
| | Part -III (Pre-lubrication/Extra-granular) | — | — | — | — |
| 9 | Croscarmellose Sodium | 4 | 2 | 2 | 1.94 |
| | Part-IV (Lubrication/Extra-granular) | — | — | — | — |
| 10 | Magnesium Stearate | 1.5 | 0.75 | 0.75 | 0.73 |
| | Total Weight of Core Tablet | 200 | 100 | 100 | — |
| | Part -V (Coating) | — | — | — | — |
| 11 | Opadry Pink/yellow | 6 | 3 | — | 2.91 |
| 12 | Purified Water* | q.s. | q.s. | — | — |
| | Total Weight of Coated Tablet | 206 | 103 | — | 100 |

*Removed during processing & only traces will be present in final product. Manufacturing process:

a) Part-I (Dry Mix): Apixaban. MCC, Lactose Anhydrous, Croscarmellose sodium were sifted through #40 sieve and mixed to prepare the dry mix.
b) Part-II: Sodium lauryl sulphate and Povidone K-25 were dissolved in water. Apixaban was dispersed in obtained solution. This dispersion was sprayed on dry mix prepared in step a) in RMG to prepare the granules.
c) Drying and sizing: Granules were dried in rapid dryer for 15 minutes and sized using #30 sieve.
d) Pre-Lubrication: Croscarmellose Sodium was sifted through # 40 sieve and in Double Cone Blender, sized granules prepared in step c) were pre-Lubricated to prepare pre-lubricated blend.
e) Lubrication: Magnesium Stearate was sifted through # 60 sieve and pre-lubricated blend prepared in step d) was lubricated to prepare lubricated blend.
f) Compression: Lubricated blend prepared in step e) was compressed into tablets using appropriate punch set.
g) Coating: Compressed tablets prepared in step f) were coated by Opadry pink/yellow suspension to achieve required weight gain for different strengths.

We claim:

1. A pharmaceutical composition comprising apixaban having a $D_{90}$ particle size range of about 350 microns to about 800 microns, a diluent which is a mixture of microcrystalline cellulose and lactose, a surfactant which is sodium lauryl sulphate, a disintegrant which is croscarmellose sodium, and a lubricant which is magnesium stearate; wherein the composition is a binder-free composition and an immediate release composition wherein at least 75 wt % of apixaban dissolves within 30 minutes in a pH 6.8 phosphate buffer containing 0.05% sodium lauryl sulfate.

2. The pharmaceutical composition according to claim 1, wherein the composition further comprises one or more pharmaceutically acceptable excipients selected from the group consisting of a glidant, a coating agent, a plasticizer, a coloring agent, and a viscosity enhancer.

3. The pharmaceutical composition according to claim 1, wherein the composition is in a dosage form selected from the group consisting of tablet, capsule, powder, caplet, granules, pellets, tablet in tablet, tablet in capsule, pellets in capsule, powder in capsule, and granules in capsule.

4. The pharmaceutical composition according to claim 1, wherein the composition is a tablet.

5. The pharmaceutical composition according to claim 1, wherein the composition is prepared in a tablet form by:

co-sifting a diluent and a disintegrant through a sieve to prepare a dry mix;

dissolving apixaban having a $D_{90}$ particle size range of about 350 microns to about 800 microns in an organic solvent to prepare a drug solution;

spraying the drug solution onto the dry mix in a fluidized bed processor to produce drug granules;

drying the drug granules in a fluidized bed processor to produce dried drug granules; spraying a solution of a surfactant onto the dried drug granules to produce surfactant coated drug granules;

drying the surfactant coated drug granules in a fluidized bed processor to prepare dried surfactant coated drug granules;

sifting the dried surfactant coated drug granules through a sieve to produce sifted granules;

pre-lubricating the sifted granules to produce an extra-granular pre-lubricated blend;

lubricating the extragranular pre-lubricated blend with a lubricant to produce a lubricated blend; and compressing the lubricated blend to produce an uncoated tablet; and optionally coating the uncoated tablet.

* * * * *